United States Patent
Parvaneh et al.

(10) Patent No.: US 11,800,996 B2
(45) Date of Patent: Oct. 31, 2023

(54) SYSTEM AND METHOD OF DETECTING FALLS OF A SUBJECT USING A WEARABLE SENSOR

(71) Applicant: KONINKLIJKE PHILIPS N.V., Eindhoven (NL)

(72) Inventors: Saman Parvaneh, Danvers, MA (US); Ali Akbar Ahmad Samadani, Somerville, MA (US)

(73) Assignee: Koninklijke Philips N.V., Eindhoven (NL)

( * ) Notice: Subject to any disclaimer, the term of this patent is extended or adjusted under 35 U.S.C. 154(b) by 465 days.

(21) Appl. No.: 16/992,206

(22) Filed: Aug. 13, 2020

(65) Prior Publication Data

US 2021/0052198 A1    Feb. 25, 2021

Related U.S. Application Data (60) Provisional application No. 62/889,289, filed on Aug. 20, 2019.

(51) Int. Cl.
*A61B 5/11* (2006.01)
*A61B 5/0205* (2006.01)

(52) U.S. Cl.
CPC .......... *A61B 5/1117* (2013.01); *A61B 5/0205* (2013.01); *A61B 5/1118* (2013.01)

(58) Field of Classification Search
CPC ... A61B 5/1117; A61B 5/0205; A61B 5/1118; G08B 21/0423; G08B 21/0446;
(Continued)

(56) References Cited

U.S. PATENT DOCUMENTS

| 6,166,639 A | 12/2000 | Pierce |
| 8,810,388 B2 | 8/2014 | Jacobs |

(Continued)

FOREIGN PATENT DOCUMENTS

| CA | 2990529 A1 | 6/2018 |
| JP | 2013092923 A | 5/2013 |

(Continued)

OTHER PUBLICATIONS

Belin, et al "The Montreal Affective Voices: A Validated Set of Nonverbal Affect Bursts for Research on Auditory Affective Processing", Behavior Research Methods, vol. 40, No. 2, pp. 531-539. 2008.

(Continued)

*Primary Examiner* — Eric F Winakur
*Assistant Examiner* — Emily C Clement (57) ABSTRACT

A system and method are provided for performing physical activity monitoring and fall detection of a subject using a wearable sensor including at least one audio sensor and at least one of an accelerometer, a gyroscope and a magnetometer. The method includes monitoring activities of the subject using the at least one of the accelerometer, the gyroscope and the magnetometer, and identifying a characteristic motion pattern based on the monitored activities; detecting an apparent fall experienced by the subject based on the identified at least one characteristic motion pattern; monitoring sounds provided by the at least one audio sensor following the detected apparent fall; determining whether the detected apparent fall is an actual fall experienced by the subject based on the monitored sounds; and communicating an indication of the actual fall to a monitoring system, enabling commencement of responsive action.

18 Claims, 5 Drawing Sheets

(58) Field of Classification Search
CPC ............ G08B 21/0469; G08B 21/0476; G08B 25/001; G08B 25/016; G08B 25/10; G08B 21/043
See application file for complete search history.

(56) References Cited

U.S. PATENT DOCUMENTS

| | | | |
|---|---|---|---|
| 9,900,718 | B2 | 2/2018 | Goldstein |
| 10,629,048 | B2 * | 4/2020 | Tan ..................... G01S 19/13 |
| 11,031,013 | B1 * | 6/2021 | Myers ................. G10L 15/1822 |
| 2001/0020898 | A1 | 9/2001 | Pierce |
| 2009/0322513 | A1 | 12/2009 | Hwang |
| 2014/0077946 | A1 | 3/2014 | Tran |
| 2014/0266690 | A1 | 9/2014 | McKinley et al. |
| 2015/0145661 | A1 | 5/2015 | Beggs et al. |
| 2015/0145662 | A1 * | 5/2015 | Barfield, Jr. ....... G08B 21/0492 340/436 |
| 2015/0269825 | A1 | 9/2015 | Tran |
| 2017/0215835 | A1 * | 8/2017 | Sezan .................. A61B 7/026 |
| 2017/0319082 | A1 | 11/2017 | Sayme |
| 2020/0365275 | A1 * | 11/2020 | Barnett ............... A61B 5/4088 |
| 2021/0005067 | A1 * | 1/2021 | Salekin ................. G10L 25/30 |

FOREIGN PATENT DOCUMENTS

| | | | |
|---|---|---|---|
| WO | WO-2015047873 A2 * | 4/2015 | .......... A61B 5/0245 |
| WO | 2017017547 A1 | 2/2017 | |
| WO | 2018046595 A1 | 3/2018 | |

OTHER PUBLICATIONS

Administration on Aging (AoA) (2014). A Profile of Older Americans. http://www.aoa.acl.gov/Aging_Statistics/Profile/index.aspx. Retrieved Aug. 11, 2015.
Federal Interagency Forum on Aging-Related Statistics. 2012. Older Americans 2012: Key Indicators of Well-Being, 60.
Guerriero, F. et al, "Pain management in dementia: so far, not so good." Vascular 64 (2016), pp. 31-39.
Salva, Antoni et al, "Incidence and consequences of falls among elderly people living in the community". Medicina Clinica, vol. 122, Issue 5, pp. 172-176, 2004, Abstract Only.
Milat, Andrew J. et al, "Prevalence, circumstances and consequences of falls among community-dwelling older people: results of the 2009 NSW Falls Prevention Baseline Survey", NSW Public Health Bulletin, vol. 22, No. 3-4, pp. 43-48, 2011.

* cited by examiner

SYSTEM AND METHOD OF DETECTING FALLS OF A SUBJECT USING A WEARABLE SENSOR

CROSS-REFERENCE TO PRIOR APPLICATIONS

This application claims the benefit of U.S. Provisional Patent Application No. 62/889,289, filed Aug. 20, 2019, which is incorporated by reference herein.

BACKGROUND

The aging population is at a higher risk of fall, resulting in a wide range of adverse conditions ranging from general ambulatory decline to serious physical disabilities. Conventional accelerometric detection of falls has been widely used for ambulatory tracking and fall detection in personal emergency response systems (PERSs). Despite technological advancements in accelerometric techniques, there is still room for improvement, particularly with regard to improving PERS ability to detect a user's fall-related pain level, and reducing false-positives.

More particularly, the population ages 65 years and older in the United States in 2014 was about 46.2 million people, an increase of about 28 percent from 2004, and is projected to grow to about 82.3 million people by the year 2040. Within this group, the population ages 85 years and older is projected to triple from about 6.2 million in 2014 to about 14.6 million in 2040. A vast majority of the older population appear to be aging in place (i.e., staying in their homes and communities. For example, in the United States, about 93 percent of Medicare beneficiaries ages 65 years and older) are aging in place, and in Canada, about 92 percent of individuals ages 65 and older are aging in place. This burgeoning older population in in need of technologies that enable independent and healthy living while aging in place.

Falls are among main etiologies for adverse and life-limiting physical disabilities in older populations. For example, each year, about one third of the adults ages 65 and older experience at least one fall with up to about 15 percent of these falls leading to serious injuries and death. PERS, such as Philips Lifeline, for example, aim to enable independent and safe aging-in-place by providing continuous monitoring of user mobility and automatically detecting falls, and delivering emergency care when needed. PERSs typically track the user's activities and mobility state using inertial measurement units (IMUs) generally comprising an accelerometer, gyroscope, and a magnetometer. These systems can always benefit from more accurate detection models robust to non-fall positives (i.e., false events such as sitting in a deep chair). In addition to detecting fall events, it is important to build a user-aware PERS, where user's pain level resulting from a fall can be automatically assessed and necessary care dispatched, accordingly. This is particularly important for the aging population with cognitive impairments where pain is generally undertreated. So, despite advancements in PERS technologies, estimation of user pain level and intensity following a fall event is generally insufficiently accurate.

In addition to fall detection, PERs may be used to measuring physical activity of the user, for example, using the IMUs. Measuring physical activity may be challenging as the IMUs measure physical activity when worn, and a minimum amount of wear time is required for valid assessment of physical activity. Wear time by the user must be identified to differentiate between when the user is performing no activity (i.e., sedentarism) while wearing the PERS monitor versus when the user simply is not wearing the PERS monitor, for example, during bathing and sleeping. Conventional PERs may also collect information on vital signs, such as heart rate and heart rate variability with IMU information. Typical sources for measuring heart rate and heart rate variability are electrocardiogram (ECG) monitors attached to the user's chest using electrodes and photoplethysmography (PPG). However, measuring ECG is inconvenient for long-term monitoring and accurate PPG assessments require close contact between a light source/detector and the user's skin, which again may be inconvenient.

Therefore, an efficient approach is needed to evaluate human physical activities and postures of a subject using a wearable sensor, to detect when the wearable sensor is not being worn, and to detect and verify a fall event using the wearable sensor.

SUMMARY

According to an aspect of the present disclosure, a method is provided for performing physical activity monitoring and fall detection of a subject using a wearable sensor including at least one audio sensor and at least one of an accelerometer, a gyroscope and a magnetometer. The method includes monitoring activities of the subject using the at least one of the accelerometer, the gyroscope and the magnetometer, and identifying a characteristic motion pattern based on the monitored activities; detecting an apparent fall experienced by the subject based on the identified at least one characteristic motion pattern; monitoring sounds provided by the at least one audio sensor following the detected apparent fall; determining whether the detected apparent fall is an actual fall experienced by the subject based on the monitored sounds; and communicating an indication of the actual fall to a monitoring system, enabling commencement of responsive action.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only and is not intended to be limiting. As used in the specification and appended claims, the singular forms of terms "a", "an" and "the" are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Various embodiments of the present disclosure provide systems, methods, and apparatus for auditory, accelerometric and heart-rate-based detection of falls, intensity of falls, and fall-related pain experiences of a user. The multimodal approach improves fall detection accuracy and enables estimating the intensity of fall using post-fall sound signals. The sounds signals contain auditory cues associated with the pain level of the user, and hence may indicate the severity and intensity of the fall. In the various embodiments, audio sensors (e.g., one or more microphones) are activated and scan surroundings for sounds after an initial accelerometric detection of a fall. The sound signals include acoustic and prosodic (voiced and unvoiced) cues, as well as heart sounds from which the post-fall heart rate of the user may be extracted, enabling more precise and sensitive fall detection, automatic monitoring of pain-related cues, and thus more efficient and user-aware urgent care.

Various embodiments focus on estimation of fall-related pain of the user from acoustic, prosodic and cardiographic manifestations of that pain. Thus, audio sensors, such as microphones, may be included in PERS devices to scan for pain-related acoustic and prosodic cues, such as sighing, moaning and groaning, for example. In addition, since the PERS pendants are positioned on the user's chest, the user's heart rate may be acoustically monitored, as well as accelerometrically monitored. Changes in the user's heart rate and heart rate variability are likewise indicative of the level of fall related pain. By estimating the pain level associated with a fall event, urgent care may be delivered accordingly, promoting more user-aware and response-efficient PERS technologies.

Figure 1:
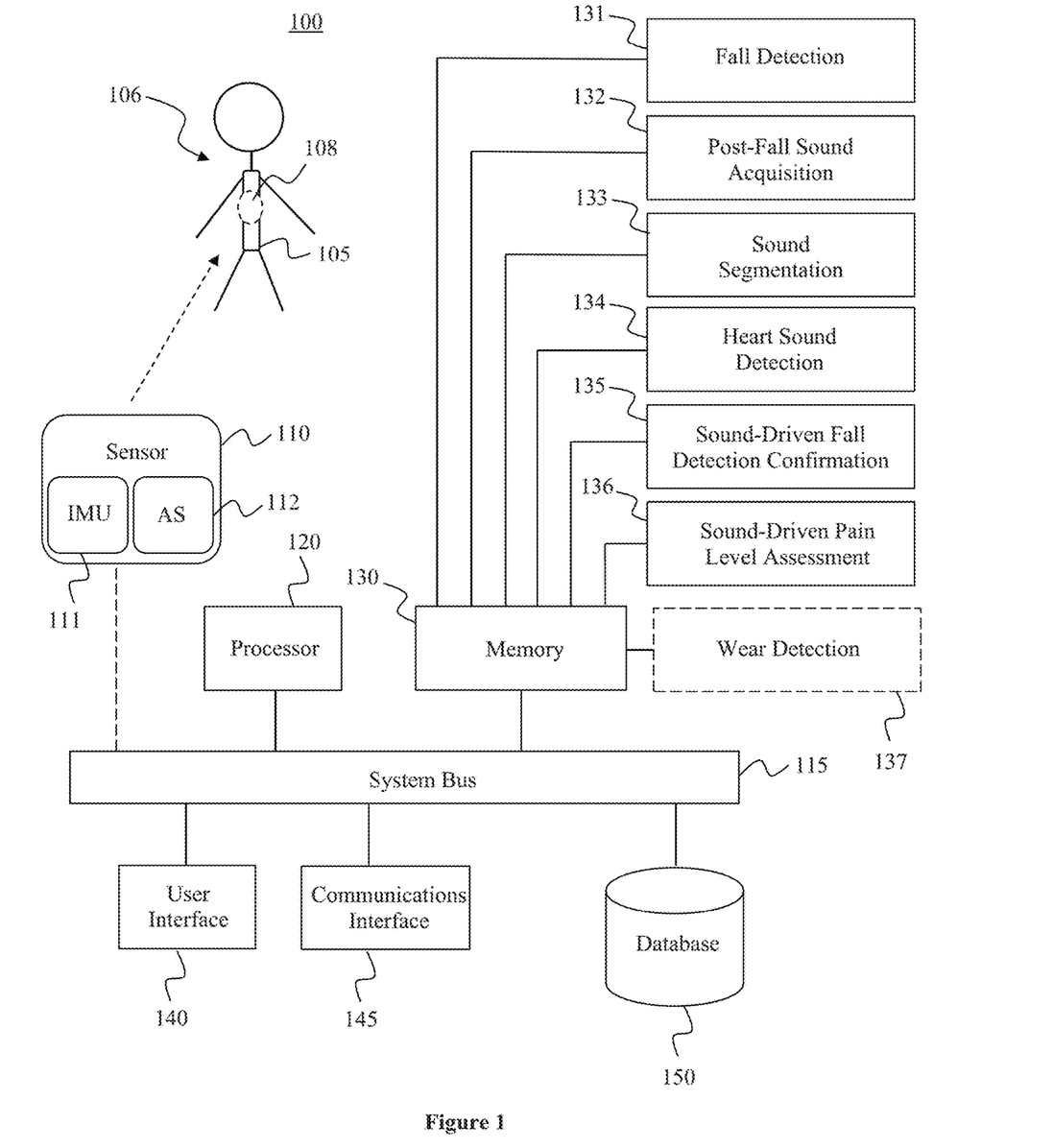
FIG. 1 illustrates a simplified block diagram of a system configured for activity monitoring and fall detection of a subject using a wearable sensor, in accordance with a representative embodiment.

FIG. 1 illustrates a simplified block diagram of a system configured for performing physical activity monitoring and fall detection of a user of a wearable sensor, in accordance with a representative embodiment.

Referring to FIG. 1, a sensor 100 configured to execute the methods described herein for evaluating a subject 106 includes a wearable sensor 110 that is physically located on the body 105 of the subject 106. The wearable sensor 110 may be any device attachable to the body 105 for collecting data by monitoring one or more characteristics of the body 105. In the depicted embodiment, the wearable sensor 110 includes an inertial measurement unit (IMU) 111 and one or more audio sensors, indicated by representative audio sensor 112. The IMU 111 includes an accelerometer, a gyroscope and/or magnetometer, which are used generally to detect movement (and lack of movement) of the body 105. The IMU 111 is configured to track ambulatory physical activities of the subject 106, and to capture or identify characteristic motion patterns of the body 105 indicative of various events, including reclining, sitting, standing, walking and falling, for example. The characteristic motion patterns may be identified by comparison to models of the characteristic motion patterns previously stored in database 150, for example, for comparison with data provided by the IMU 111 corresponding to the tracked physical activities. Notably, the characteristic motion patterns may also be identified using classification models pre-trained on a wide range of motion signals corresponding to different characteristic motions. The audio sensor 112 may include one or more microphones, or other device or array of devices capable of detecting sound signals. The audio sensor 112 scans surroundings for acoustic/prosodic voiced and unvoiced (silent) portions of the acoustic observations succeeding a detected fall event. In various embodiments, the audio sensor 112 may be activated continuously when the wearable sensor 110 is activated, or the audio sensor 112 may be selectively activated, for example, only upon detection of a fall or apparent fall using the IMU 111. The wearable sensor 110 may be a commercial wearable device, such as a Philips Lifeline wearable on the chest 108 of the subject 106, for example. Alternatively, certain types of fitness monitoring devices are contemplated. These devices are often worn on the user's wrist, and by the present teachings can be adapted for use in fall detection as well as desired types of activity tracking. These illustrative activity tracking devices are contemplated to be used to collect post-fall sounds using an embedded microphone in the wristband device, with the difference that the wristband would measure heart rate directly rather than through heart sounds as is done by a chest-worn device. Still alternatively, rather than a chest-worn or wrist-worn activity tracker, a neck-worn device that sits tight laterally around the neck is contemplated. The data may be collected by the wearable sensor 110 itself, as well as by remote sensors (not shown) at various remote locations on the body 105 or ambient sensors around the room apart from the wearable sensor 110, the remote sensors being in communication with the wearable sensor 110 through wireless and/or wired connections. Notably, ambient sensors contemplated by the present teachings include, but are not limited to various pressure sensors, including for collector sensors, such as piezoelectric sensors, microphones, RADAR sensors and light detection and ranging (LiDAR) sensors. As will be appreciated, these ambient sensors can readily determine the location of a user, as well as changes in location of the user. Further, these ambient sensors may determine user's posture (e.g., standing, lying prone or supine, walking, sitting, sleeping).

The sensor 100 may further include, for example, a processor 120, memory 130, user interface 140, communication interface 145 and the database 150 interconnected via at least one system bus 115. It is understood that FIG. 1 constitutes, in some respects, a simplified abstraction and that the actual organization of the components of the sensor 100 may be more complex than illustrated. Further, the wearable sensor 110 is shown connected to the system bus 115 by a dashed line, indicating that any combination of all or some of the processor 120, the memory 130, the user interface 140, the communication interface 145 and the database 150 may be incorporated into the wearable sensor 110 itself, worn on the body 105 of the subject 106. For example, in an embodiment, the processor 120, the memory 130, the user interface 140 and the communication interface 145 may be located in the wearable sensor 110, enabling localized processing of data collected by the wearable sensor 110, while the database 150 may be located in a remote server(s) accessible to the wearable sensor 110 by a wireless network or wireless connection via the communication interface 145. Alternatively, in another embodiment, the communication interface 145 may be located in the wearable sensor 110, along with basic processing and user interfacing capability to enabling basic communications, such as sending out the collected data and receiving processing results. Meanwhile, the processor 120, the memory 130 and the database 150 may be located in a remote server(s) accessible to the wearable sensor 110 by a wireless network or wireless connection via the communication interface 145, enabling remote processing of the raw data collected by the wearable sensor 110. This embodiment may allow for more efficient processing and expanded storage. Other combinations of locations for the processor 120, the memory 130, the user interface 140, the communication interface 145 and the database 150, including dividing of respective functionalities, between local and remote locations may be incorporated without departing from the scope of the present teachings.

The processor 120 may be any hardware device capable of executing instructions stored in memory 130 and the database 150, and otherwise processing raw data. As such, the processor 120 may include a microprocessor, field programmable gate arrays (FPGAs), application-specific integrated circuits (ASICs), or other similar devices, as discussed below with regard to processor 510 in illustrative computer system 500 of FIG. 5. The processor 120 may execute the instructions to implement part or all of methods described herein. Additionally, the processor 120 may be distributed among multiple devices, e.g., to accommodate methods necessarily implemented in a distributed manner that requires multiples sets of memory/processor combinations.

The memory 130 may include various memories such as, for example, cache or system memory. As such, the memory 130 may include static random-access memory (SRAM), dynamic RAM (DRAM), flash memory, read only memory (ROM), or other similar memory devices, as discussed below with regard to main memory 520 and/or static memory 530 in illustrative computer system 500 of FIG. 5. It will be apparent that, in embodiments where the processor includes one or more ASICs (or other processing devices) that implement one or more of the functions described herein in hardware, the software described as corresponding to such functionality in other embodiments may be omitted. That is, the memory 130 may store instructions for execution by the processor 120 and/or data upon with the processor 120 may operate.

The user interface 140 may include one or more devices for enabling communication with a user, such as the subject 106, a family member, a caregiver, a clinician, a technician, a doctor and/or other medical professional, for example. In various embodiments, the user interface 140 may be wholly or partially included on the wearable sensor 110, as mentioned above, for immediate access by the subject 106, and may include a display and keys, buttons and/or a touch pad or touch screen for receiving user commands. Alternatively, or in addition, the user interface 140 may include a command line interface or graphical user interface that may be presented to a remote terminal via the communication interface 145. Such remote terminal may include a display, a touch pad or touch screen, a mouse, and a keyboard for receiving user commands.

The communication interface 145 (e.g., network interface) may include one or more devices enabling communication by the wearable sensor 110 with other hardware devices. For example, the communication interface 145 may include a network interface card (NIC) configured to communicate according to the Ethernet protocol. Additionally, the communication interface 145 may implement a TCP/IP stack for communication according to the TCP/IP protocols, enabling wireless communications in accordance with various standards for local area networks, such as Bluetooth (e.g., IEEE 802.15) and Wifi (e.g., IEEE 802.11), and/or wide area networks, for example. Various alternative or additional hardware or configurations for the communication interface 145 will be apparent.

The database 150 may include one or more machine-readable non-transitory storage media such as read-only memory (ROM), random-access memory (RAM), magnetic disk storage media, optical storage media, flash-memory devices, or similar storage media. In various embodiments, the database 150 may store instructions for execution by the processor 120 or data upon with the processor 120 may operate (alone or in conjunction with the memory 130). For example, the database 150 may store one or more models for activity and posture recognition as well as fall detection. Generally, each of the models is trained based on training data acquired by a sensor mounted on the chest of training subjects, or a simulation of the same. Models are trained and their performance is verified through various resampling of the training data, where the data are generally divided into train, validation, and test sets. The train data are used to build the model, the validation data are used to tune the hyper parameters of the model and to optimize the model performance on the validation set. The test data are completely left-out during the training phase, and are used to verify the performance of the trained model on a previously-unseen data. Each of the models may include processor executable instructions for determining physical activities and postures based on the training data as applied to the model. The models may be recurrent neural network models with Long Short-Term Memory (LSTM) units, for example.

The memory 130 may include various modules, each of which comprises a set of related processor executable instructions corresponding to a particular function of the sensor 100. For example, in the depicted embodiment, the memory 130 includes fall detection module 131, post-fall sound acquisition module 132, sound segmentation module 133, heart sound detection module 134, sound-driven fall detection confirmatory module 135, sound-driven pain level assessment module 136, and an optional wear detection module 137. In an embodiment, the memory 130 may further include an optional battery optimization module (not shown).

The fall detection module 131 includes processor executable instructions for detecting an apparent fall experienced by the subject 106. The fall detection module 131 receives data from the IMU 111, for example, from monitoring activities of the body 105. The fall detection module 131 identifies characteristic motion patterns of the subject 106 based on the received data, and detects an apparent fall when the characteristic motion pattern is consistent with a fall. That is, the fall detection module 131 receives and processes accelerometric signals, extracts segments of distinct activities, and classifies each extracted segment as fall or no-fall.

The post-fall sound acquisition module 132 includes processor executable instructions for monitoring sounds provided by the audio sensor 112 following the detected apparent fall experienced by the subject 106. In an embodiment, the post-fall sound acquisition module 132 is initiated when a fall event is detected by fall detection module 131. The post-fall sound acquisition module 132 activates the audio sensor 112 to receive ambient sound signals subsequent to the detected fall event, and to scan for audible trauma-related cues, e.g., including linguistic, paralinguistic and prosodic cues, produced by the subject 106. The audio sensor 112 also acquires heart sounds of the subject 106 subsequent to the detected fall. Thus, heart related information, such as heart rate, heart rate variability and/or heart sound quality, may be determined without the use of ECG monitors attached to the subject 106 or PPG. In an embodiment, the audio sensor 112 may be implemented using multiple audio sensors, at least one of which is dedicated to acquiring ambient sounds and at least another one of which is dedicated to acquiring heart sounds, without departing from the scope of the present teachings. The at least one audio sensor that acquires heart sounds may include a microphone facing inward toward the chest of the subject 106, for example. In an embodiment, the audio sensor 112 also acquires heart sounds of the subject 106 whenever the subject 106 is wearing the audio sensor 112, including prior to a detected fall and regardless of whether a fall is detected.

The sound segmentation module 133 includes processor executable instructions for isolating pain related sound signals from the sound signals acquired by the post-fall sound acquisition module 132. Generally, the sound segmentation module 133 receives the acquired sound signals, and isolates those sound signals corresponding to sounds that are produced by the subject 106, for example, using a model retrieved from the database 150. The model may be tuned to the acoustic profile of the subject 106. In accordance with a representative embodiment, the segmentation model is trained using annotated audio signals corresponding to trauma-related cues as well as those corresponding to no trauma events. The segmentation models may be tuned to the acoustic profile of a user by either using audio signals only from the user for training the segmentation model, or through building cohort-specific model that are trained on homogenous user base either in terms of gender, age, chronic conditions, or acoustic profile such as characteristics of user's spectral formant. The segmentation model may be updated periodically to adapt to changes in a user's profile as observed in continuously collected audio signals. The isolated sound signals are then processed to extract segments corresponding to audible trauma-related cues, which may include pain-specific verbal and acoustic cues and abnormal breathing, for example. Non-limiting examples of pain-specific verbal and acoustic cues indicative of an injury for example, which may be determined using natural language processing, include sighing, moaning and groaning; grunting; abnormal breathing; asking for help; and/or crying. Non-limiting examples of abnormal breathing include labored and noisy breathing, and wheezing; extended period of hyperventilation or tachypnea; and Cheyne-Stokes respiration.

In an embodiment, the sound segmentation module 133 provides a classifier that receives as input extracted sequences of sounds corresponding to pain-related cues, including vocalized (e.g., voiced and unvoiced) and/or verbal expressions of pain, discussed above. These pain-related cues are reported to be easily recognizable by human observers, such as those reported by Belin et al., "The Montreal Affective Voices: a validated set of nonverbal affect bursts for research on auditory affective processing," *Behavior Research Methods*, 40(2) (2008), pp. 531-539 (hereinafter "MAV"), which is hereby incorporated by reference in its entirety. For example, the pain assessment may adopt the well-known self-reported Visual Analogue Scale.

The classifier may use a hybrid approach, discussed below with reference to FIG. 3. First, a gated recurrent neural network with bi-directional LSTM units, followed by an attention layer that receives a sequence of sounds, identifies and attends to segments corresponding to pain episodes, and encodes these segments into a fixed-length representation. Second, pain-specific acoustic and prosodic characteristics relative to those included in MAC are combined with the fixed-length representation, and fed into a set of fully-connected dense layers with sigmoidal activation. The weights of this hybrid classifier may be learned during training of the classifier to optimize classification performance on a validation set.

The heart sound detection module 134 includes processor executable instructions for detecting heart sounds and determining heart related information (heart profile), such as heart rate, heart rate variability and/or heart sound quality, based on the detected heart sounds. The heart sound related sound signals may be detected from the sound signals provided by the post-fall sound acquisition module 132. In an embodiment, the heart sound detection module 134 may perform auditory-accelerometric detection of the heart rate, for example. Heart sounds may be initially captured by one or more microphones of the audio sensor 112 facing the chest of the subject 106, and the captured heart sound signals may be band pass filtered for clarity. Also, other optional microphones (not shown) of the wearable sensor 110 may be used to cancel environment noise, as well as lung sounds, using methods such as Independent Component Analysis (ICA) and/or Empirical Mode Decomposition (EMD), for example.

As mentioned above, the audio sensor 112 may be implemented to include one or more audios sensors dedicated to acquiring heart sounds. In addition, heart motions are manifested as skin vibrations generating acoustic pressure waves measurable by the audio sensor 112 (e.g., one or more microphones) positioned in close proximity to the skin in the chest and abdominal areas of the body 105. As such, the microphones are also adapted to receive both ambient sounds and skin vibrations. Further, the skin vibrations may also be picked up by the IMU 111 sitting on the skin surface at locations (e.g., chest 108) where the skin vibrations are occurring. The auditory-accelerometric detection of the heart rate scans both the acquired auditory signals and accelerometric signals for components corresponding to the two part rhythm of the heart sounds (S1-S2 heart sounds). The sensor 100 sits on the chest 108 of the subject 106 (and/or abdomen), and is thus able to pick up vibrations at chest and abdominal areas. Further, embedded microphones in the sensor 100 (and thus audio sensor) capture cardiac sounds of the subject 106, enabling estimation of subject's heart rate variability and profile subsequent to a fall event. The heart sound detection module 134 may also be configured to detect proximity of the sensor 100 to the heart of the subject 106 and quality of the heart sounds. That is, feature-based and/or deep learning may be used for heart sound quality assessment, an example of which is provided by commonly-owned International Patent Application WO2018046595A1, entitled "Classifier Ensemble for Detection of Abnormal Heart Sounds," to Parvenah, et al. The disclosure of International Patent Application WO2018046595A1 is hereby specifically incorporated by reference in its entirety. For example, the amplitude of the heart sounds (S1 and S2) may be compared with a predetermined baseline amplitudes (no pain or relaxed) for the subject 106. The difference between the heart sound amplitudes and the baseline amplitudes indicates proximity of the sensor 100 to the heart. The detected proximity of the sensor 100 to the heart may be used as a signal quality metric, where the closer the sensor 100 (and thus the audio sensor 112) is positioned with respect to the heart, the higher the signal quality. Notably, the signal quality could also be determined through measuring, for example, signal energy, signal-to-noise ratio (SNR), and correlation with past data. The signal quality is determined to be acceptable when a signal quality metric (e.g., SNR) exceeds a predetermined threshold.

When the signal quality is acceptable, the S1 sounds in heart sound will be detected and an interval between consecutive S1 sounds may be considered as the heart rate, and variations in the heart rate over a predetermined period of time are calculated as heart rate variability. The resulting heart rate and heart rate variability profile, with or without the audible trauma-related cues discussed above, may be used to confirm occurrence of an actual fall and/or to estimate the related pain experience of the subject 106, as discussed below. For example, the heart rate and the heart rate variability compared to respective baselines may be utilized for physiological-based pain assessment of the subject 106, discussed below with reference to sound-driven pain level assessment module 136.

The sound-driven fall detection confirmatory module 135 includes processor executable instructions for confirming the occurrence of a fall event, detected by the IMU-based fall detection module, e.g., using the extracted audible trauma-related cues (e.g., oral, vocal, linguistic and paralinguistic cues, and breathing abnormalities), and/or the heart rate information. The sound-driven pain level assessment module 136 similarly includes processor executable instructions for processing the extracted audible trauma-related cues (e.g., fixed-length representation of sound segments corresponding to pain episodes and MAV determination), along with the heart rate information to estimate the level of pain associated with a detected fall. Furthermore, the general health and wakefulness of the subject 106 after confirmation of the actual fall may be evaluated by the sound-driven pain level assessment module 136 using the extracted audible trauma-related cues and/or the heart rate information. The sound-driven fall detection confirmatory module 135 may also determine the severity of the detected fall based on the estimated level of pain provided by the sound-driven pain level assessment module 136.

The information about the detected fall, along with the estimated pain level, may be communicated to one or more monitoring systems, for example, by the communication interface 145, which may be a wireless interface, such as Bluetooth or Wifi, for example. The one or more monitoring systems may include an emergency dispatch center (e.g., a 911 call center, or an independent call center such as a Philips Lifeline Call Center), a PERS service center, and/or a computer, cellular phone, or other networked device of a caregiver of the subject 106. Additional information regarding the heart rate, the heart rate variability, and/or the heart rate quality may be communicated to the monitoring system as well. The transmitted information may assessed by an agent or caregiver who accesses the monitoring system, and depending on the level of estimated pain and severity of the fall, interventional actions may be employed accordingly (e.g., dispatch of emergency care). In addition, a message may be generated and delivered to the caregiver notifying them of the fall and subsequent physiological health and pain level. The information may also be stored for assessment of the health of the subject 106, which may be used over time for diagnostic purposes and early detection of mental/physical conditions (e.g., finding correlations between frequency and severity of falls and various medical conditions, such as diabetes and dementia). The information also may be used for prioritizing users according to need (i.e., fallen users with high pain levels) in the waiting list of the emergency dispatch center.

The wear detection module 137 includes processor executable instructions for detecting whether the wearable sensor 110 is being worn by the subject 106. Generally, a minimum amount of wear time is required for wearing the wearable sensor 110 to provide valid assessment of physical activity. Also, of course, the wearable sensor 110 must be worn by the subject 106 to provide the fall detection, pain level and fall severity assessments, and monitoring system notification, described above. Further, determining wear time is important in order to differentiate between no detected activity by the subject 106 due to lack of motion (i.e., sedentarism) by the subject 106 while wearing the wearable sensor 110, versus no detected activity by the subject 106 due to the subject 106 simply not wearing the sensor (e.g., while bathing or sleeping).

It will be apparent that information described as being stored in the database 150 may be additionally or alternatively stored in the memory 130. That is, although depicted separately, the database 150 may be included in the memory 130. In this respect, the memory 130 may also be considered to constitute a "storage device" and the database 150 may be considered "memory." Various other arrangements will be apparent. Further, the memory 130 and the database 150 each may be considered to be "non-transitory machine-readable media." As used herein, the term "non-transitory" will be understood to exclude transitory signals but to include all forms of storage, including both volatile and non-volatile memories.

While the sensor 100 is shown as including one of each described component, the various components may be duplicated in various embodiments. For example, the processor 120 may include multiple microprocessors that are configured to independently execute the methods described herein or are configured to perform steps or subroutines of the methods described herein such that the multiple processors cooperate to achieve the functionality described herein. Further, where portions of the sensor 100 is implemented in a cloud computing system, the various hardware components may belong to separate physical systems. For example, the processor 120 may include a first processor in a first server and a second processor in a second server.

Figure 2:
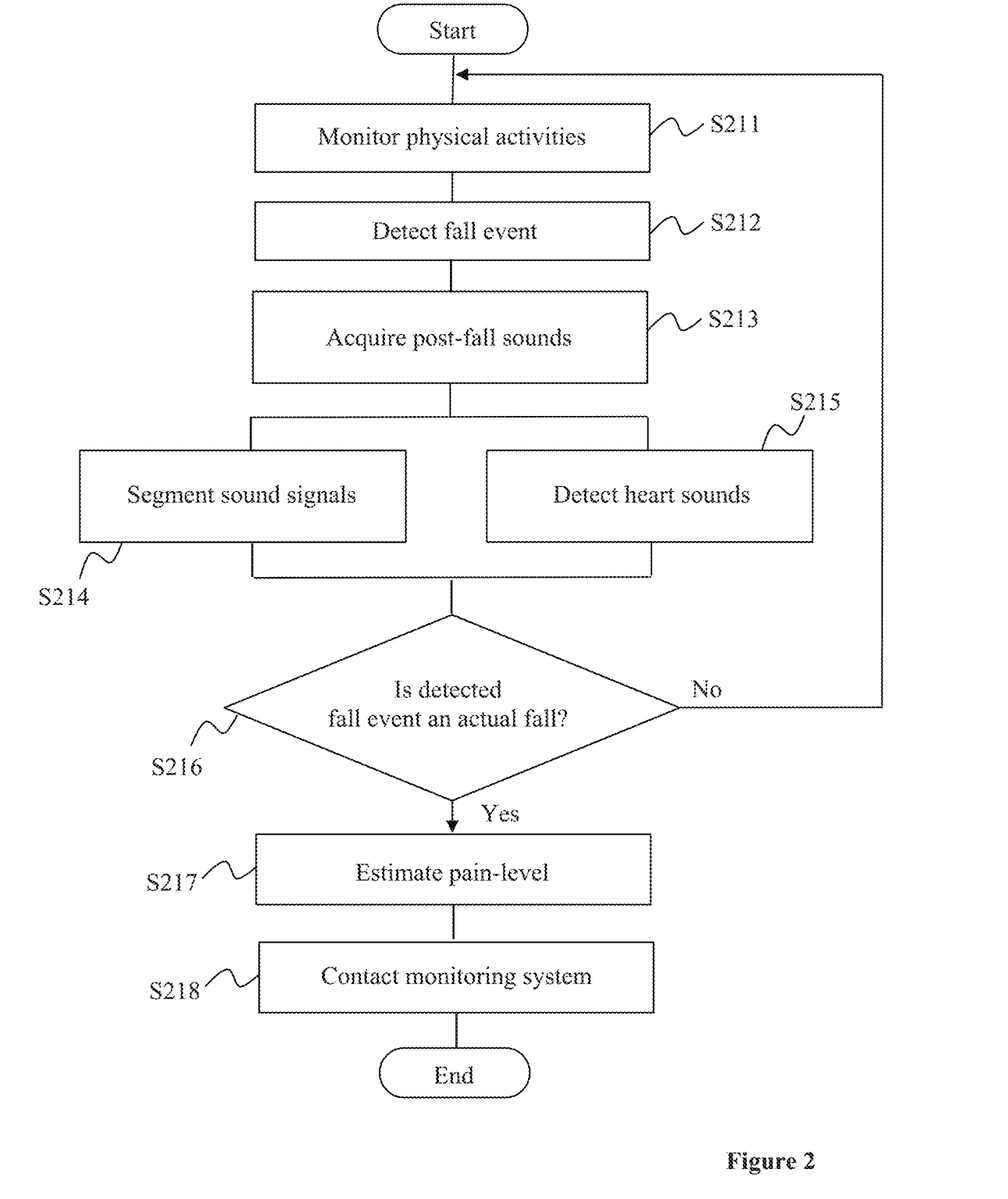
FIG. 2 illustrates a simplified flow diagram of a process for physical activity monitoring and fall detection of a subject using a wearable sensor, in accordance with a representative embodiment.

FIG. 2 is a flowchart showing a process for performing physical activity monitoring and fall detection of a subject using a wearable sensor. The sensor includes one or more audio sensors (e.g., microphones) and an IMU (e.g., at least one of an accelerometer, a gyroscope and a magnetometer), and may be worn on the body of the subject, at or near the chest or abdomen.

Referring to FIG. 2, all or a portion of the steps may be performed by the processor 120 together with the memory 130 (and associated modules), and the database 150 in FIG. 1, for example. In block S211, physical activities of the subject are monitored using the IMU in the sensor, and at least one characteristic motion pattern is identified based on the monitored activities. The characteristic motion patterns correspond to various known events, models of which may be retrieved from a database. In block S212, a fall event is detected based on identifying the characteristic motion patterns, where the detected fall event is considered an apparent fall experienced by the subject, subject to confirmation, discussed below.

Following the detected fall event, post-fall sounds are acquired as sound signals in block S213. The post-fall sounds include ambient sounds provided by the audio sensor (s), which include linguistic, paralinguistic and prosodic cues produced by the subject, for example, subsequent to the detected fall event. In an embodiment, the audio sensor(s) is activated after the fall event is detected. The post-fall sounds also include acquires heart sounds of the subject following the detected fall event. The sound signals from the heart sounds may be acquired by the same audio sensor(s) that acquires the ambient sounds, or by a dedicated heart sound audio sensor(s) (e.g., facing inward toward the chest of the subject), without departing from the scope of the present teachings.

The sound signals acquired in block S213 are processed in blocks S214 and S215. In block S214, the sounds produced by the subject are isolated from the sound signals, and sound segments corresponding to audible trauma-related cues are extracted from the isolated sound signals. Trauma-related cues may include pain-specific verbal and acoustic cues and abnormal breathing, for example, as discussed above. The sounds produced by the subject may be isolated from the acquired sound signals using a model tuned to an acoustic profile of the subject, such as the illustrative model described above. In block S215, heart information (heart profile) is detected, including heart rate, heart rate variability and/or heart sound quality, based on the sound signals acquired in block S213. To the extent that the sound signals are acquired by different audio sensors established to receive the ambient sound signals and heart sound signals, respectively, determinations of pain related sounds and the heart rate information may be made using corresponding dedicated sound data. In an embodiment, detecting the heart information may include auditory-accelerometric detection of the heart rate, as discussed above, where heart sounds and/or skin vibrations are captured by one or more microphones and/or accelerometers positioned in close proximity to the heart.

In block S216, it is determined whether the detected fall event (apparent fall) is an actual fall experienced by the subject based, at least in part, on the extracted sound segments from block S214 and/or the heart sound information from block S215. When the detected apparent fall is determined not to be an actual fall (block S216: No), the process returns to block S211 to continue monitoring of the activities of the subject. When the detected fall event is determined to be an actual fall (block S216: Yes), thereby confirming occurrence of the fall event, pain level experienced by the subject following the fall is estimated in block S217 and a monitoring system is contacted in block S218 to commence responsive action.

The determination of whether the detected fall event is an actual fall may be made by analyzing the audible trauma-related cues extracted from the sound signals in block S214, and/or the heart rate features identified in the sound signals in block S215. The post-fall trauma-related cues may be detected automatically using the sound-driven pain level assessment module 136. A detection of trauma or pain cues indicates the subject 106 may be distressed, which may, in turn, confirm occurrence of an actual fall. In another embodiment, a list of audible trauma-related cues may be provided with corresponding weights, where the weighted detection of each of the audible trauma-related cues may be summed and compared to a predetermined pain threshold for indicating an actual fall. Also, the detected apparent fall may be determined to be an actual fall when the audible trauma-related cues indicate a prolonged silence (which may result from unconsciousness) exceeding a predetermined silence threshold. Similarly, a detected heart rate or variability in heart rate may be deemed indicative of a fall when compared to corresponding baselines. For example, the detected apparent fall may be determined to be an actual fall when the heart rate of the subject exceeds a predetermined heart rate baseline and/or when the heart rate variability of the subject falls below a predetermined heart rate variability threshold. This is because it is anticipated that the subject would maintain an unusually high, steady heart rate immediately following an actual fall. In addition, a confidence level may be assigned to the initial detection of the fall event by the inertial measurement unit (e.g., including an accelerometer, a gyroscope and/or magnetometer) As such, the IMU-based fall detection module is adapted to operate independently of the post-fall pain and heart rate monitors.

Similarly, in block S217, the pain level experienced by the subject is estimated based at least in part on the audible trauma-related cues extracted from the sound signals in block S214, and/or the heart rate features identified in the sound signals in block S215. This is done using the sound-driven pain level assessment module 136, which is used to estimate the pain level in the user via audio and heart signals, as described above.

An indication to the effect that an actual fall has occurred, as well as an indication of the severity of the estimated pain level and/or the corresponding severity of the fall, are communicated to one or more monitoring systems in block S218, enabling commencement of responsive action. As discussed above, the one or more monitoring systems may include an emergency dispatch center (e.g., a 911 call center), a PERS service center, and/or a computer, cellular phone, or other networked device of a caregiver. In addition, the subject may be prompted to contact the monitoring system themselves, again enabling commencement of responsive action. The indications may include information about the subject and the fall displayed on a display of a remote terminal, e.g., in an emergency dispatch center, received at least in part via a wireless transmission from the wearable sensor. For example, the displayed information may include any combination of the subject's name, address and/or present location, severity of pain being experienced by the subject (e.g., according to a predetermined scale), heart rate information, severity of the fall (e.g., according to a predetermined scale) based at least in part of the pain level and the heart rate information, the name and contact information of the subject's caregiver(s), and associated medical history of the subject.

Figure 3:
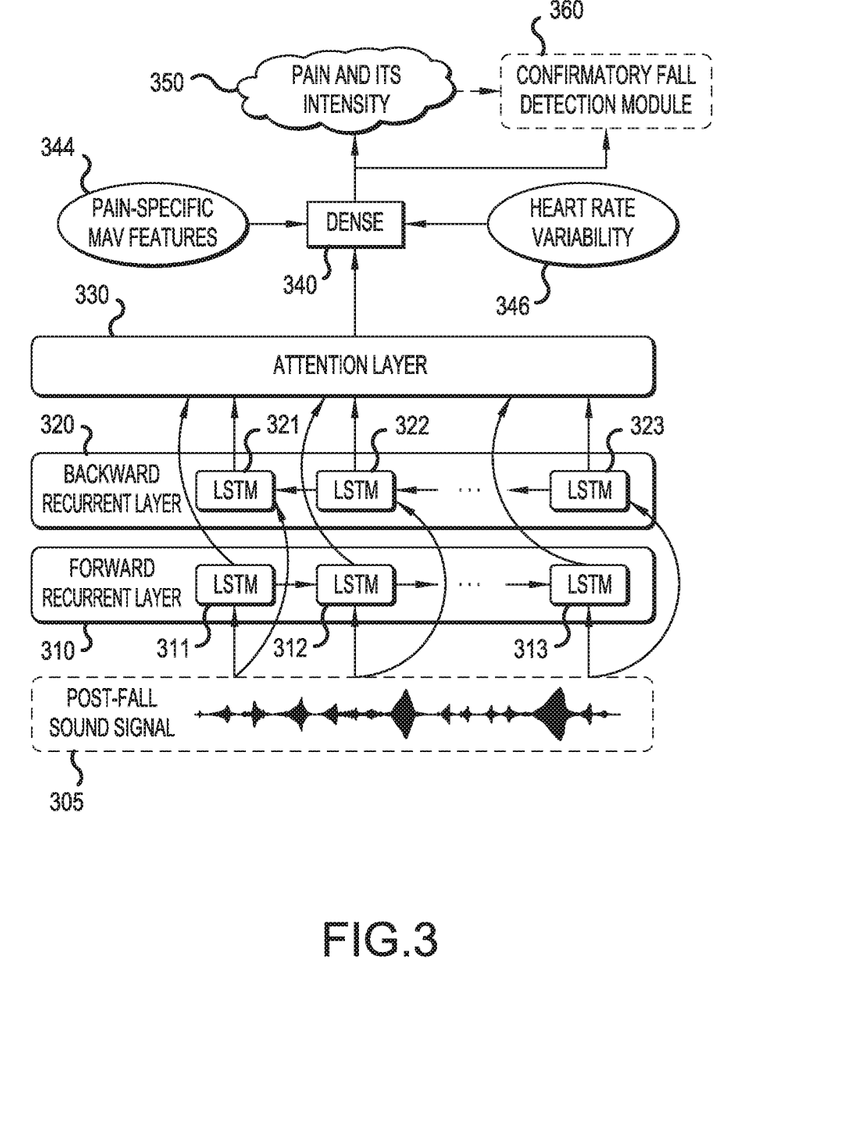
FIG. 3 is a functional block diagram showing a classification for fall confirmation and pain-level estimation, according to a representative embodiment.

FIG. 3 is a functional block diagram showing a classification for fall confirmation and pain-level estimation, according to a representative embodiment. The depicted embodiment is an example implementation of blocks S214, S216 and S217 shown in FIG. 2. However, it is understood that alternative implementations may be incorporated, without departing from the scope of the present teachings. The various blocks and associated functionalities of FIG. 3 may be implemented, for example, as sets of related processor executable instructions, respectively, stored in the memory 130 and/or the database 150, and executed by the processor 120 shown in FIG. 1.

Referring to FIG. 3, a post-fall sound signal 305 may include ambient sounds and/or heart sounds of the subject provided following the detected fall event by audio sensor(s) on the subject's body. The post-fall sound signal 305 is provided to a bi-directional, gated recurrent neutral network, including forward recurrent layer 310 and reverse recurrent layer 320. Each of the forward recurrent layer 310 and the reverse recurrent layer 320 may be a recurrent neural network that includes multiple LSTM units, where the forward recurrent layer 310 includes representative LSTM units 311, 312 and 313 for forward processing the sound signal from beginning to end, and the reverse recurrent layer 320 includes representative LSTM units 321, 322 and 323 for reverse processing the sound signal from end to beginning. The post-fall sound signal 305 is provided to each of the LSTM units 311, 312 and 313 and LSTM units 321, 322 and 323, which isolate the sound signals produced by the subject.

The output of each of the LSTM units 311, 312 and 313 and LSTM units 321, 322 and 323 is provided to attention layer 330. The attention layer 330 is a mechanism in deep neural networks that is adapted to identify features, signals and, more generally, speaking data points most salient to the classification task (i.e., in the present representative embodiment pain, no-pain). The attention layer 330 is configured to receive a sequence sounds processed by the forward and reverse recurrent layers 310 and 320, to identify and attend to segments corresponding to pain episodes, and to encodes these segments into a fixed-length representation. That is, the attention layer 330 identifies and weighs pain-related sound segments from the LSTM-processed sound signals higher than irrelevant segments, focusing on the most salient sound segments for assessing levels of pain. The attention layer 330 outputs the fixed-length representation of the pain-related sound segments to dense layer 340, which is a common name used in deep learning architecture to refer to fully-connected layers.

The dense layer 340 may be a linear transformation model. In addition to the fixed-length representation of the pain-related sound segments, the dense layer 340 receives as input pain-specific features from block 344 (e.g., a MAV database, such as database 150) and heart rate variability features from block 344 (e.g., a heart rate monitoring system, such as heart sound detection module 134). The dense layer 340 combines pain-specific acoustic and prosodic characteristics, relative to those included in the MAV database, with the fixed-length representation output by the attention layer 330. In an embodiment, the dense layer 340 may use the heart rate variability features 346 to augment data in a similar way as pain-specific MAV features. The dense layer 340 outputs a determination of pain and its intensity in block 350, and outputs a confirmation of an actual fall in block 360. Notably, the pain and pain intensity determination may be factored into the actual fall confirmation. As discussed herein, the representative embodiment shown in FIG. 3 provides an architecture which uses different layers and units known to the machine learning community and used for discriminative modeling and classification of time-series data. The specific arrangement of the layers and units including attention layer and the addition of meta-features (MAV and HRV) are illustrative examples, and are not intended to be limiting of the present teachings.

Figure 4:
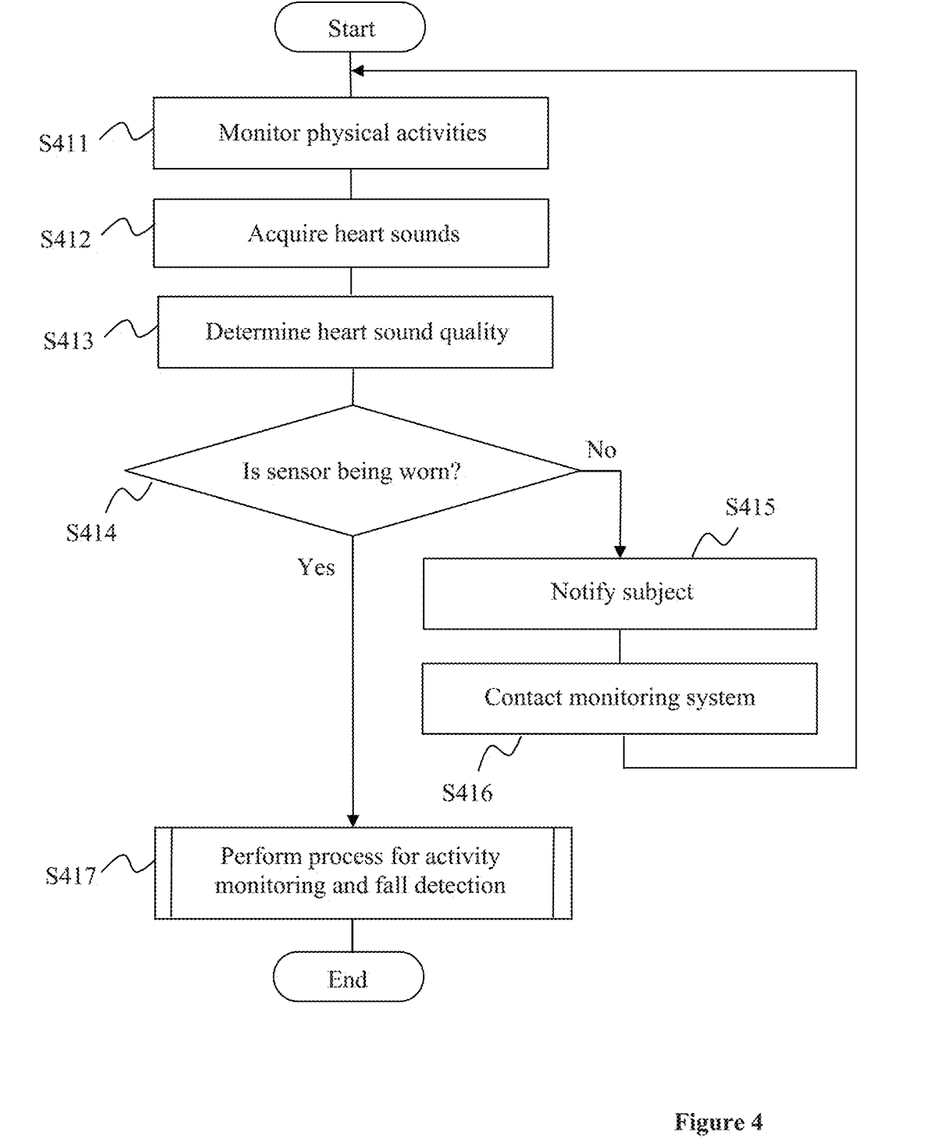
FIG. 4 illustrates a simplified flow diagram of a process for physical activity monitoring and wear detection of a wearable sensor on a subject, according to a representative embodiment.

In another aspect of the disclosure, the audio sensor(s) also may be used to determine whether the subject is wearing the sensor, based at least in part on heart sound detection, as well as for fall detection and confirmation. FIG. 4 illustrates a simplified flow diagram of a process for physical activity monitoring and wear detection of a wearable sensor on a subject, according to a representative embodiment. The sensor includes one or more audio sensors (e.g., microphones) and an IMU (e.g., at least one of an accelerometer, a gyroscope and a magnetometer), and may be worn on the body of the subject, at or near the chest or abdomen.

Referring to FIG. 4, all or a portion of the steps may be performed by the processor 120 together with the memory 130 (and associated modules, including the wear detection module 137), and the database 150 in FIG. 1, for example. In block S411, physical activities of the subject are monitored using the IMU in the sensor, and at least one characteristic motion pattern is identified based on the monitored activities. By way of illustration, in accordance with certain representative embodiments, using chest-worn pendants such as Lifeline, only fall events are detected. However, the same chest-worn IMU sensors could be used to further characterize motion patterns such as, for example, body sway, frequency and length of stride, sedentary time, and sitting/standing time. The characteristic motion patterns correspond to various known events, models of which may be retrieved from a database.

In block S412, heart sounds of the subject are acquired. Unlike the heart sound acquisition in block S213 of FIG. 2, the heart sounds are acquired in block S412 any time the subject is wearing the sensor, regardless of whether a fall event is detected. That is, the heart sounds are acquired prior and subsequent to any detected fall event. As discussed above, the sound signals from the heart sounds may be acquired by a dedicated heart sound audio sensor(s) that is facing inward toward the chest of the subject. Alternatively, the heart sounds may be acquired using the same audio sensor(s) used to detect ambient sounds, without departing from the scope of the present teachings. Other optional microphones may be used to cancel environment noise, as well as lung sounds, using methods such as ICA and/or EMD, for example. As discussed above, the heart sounds may be acquired using microphone(s) to detect actual sound signals produced by the heart and/or using sensors to detect heart motions manifested as skin vibrations, for example.

In block S413, the detected heart sounds are processed to determine heart related information, including heart rate, heart rate variability and/or heart sound quality, based on the detected heart sounds. As discussed above, the heart related information may be determined through auditory-accelerometric detection using the acquired auditory and/or accelerometric signals components corresponding to the two part rhythm of the heart sounds (S1-S2 heart sounds), for example, in order to extract S1 and S2 from the heart sounds. Inter-distance between consecutive S1s may then be extracted as the heart rate, and the heart rate variability may be determined by monitoring the extracted heart rate over a period of time, and identifying changes to the heart rate. The heart sound quality determination may include feature-based and/or deep learning, as discussed above. For example, amplitudes of detected heart sounds (S1 and S2) may be compared with previously determined baseline amplitudes for the subject. The differences between the amplitudes of the detected heart sounds and the respective bassline amplitudes indicate the proximity of the sensor to the subject's heart, as well as the signal quality of the heart sound, which generally improves the closer the sensor is to the subject's heart.

In block S414, it is determined whether the sensor is being worn by the subject based on the heart related information determined in block S413. For example, when the monitoring of physical activities in block S411 indicates sedentary behavior of the subject (e.g., little to no movement), the heart rate, the heart rate variability and/or the heart sound quality will be used to differentiate between sedentary behavior that results from inactivity by the subject while wearing the sensor versus sedentary behavior that results from the subject not wearing the sensor. For example, lack of heart rate and/or heart rate variability, and/or low heart sound quality, are features that may indicate that the subject is not wearing the sensor whenever the monitoring of the physical activities indicates sedentary behavior. For example, when the monitoring of physical activities indicates sedentary behavior, and the heart sound quality is determined to be less than a predetermined baseline of heart sound quality, it is determined that the subject is not wearing the sensor, and when the monitoring of physical activities indicates sedentary behavior, and the heart sound quality is determined to exceed the predetermined baseline of heart sound quality, it is determined that the subject is wearing the sensor. With regard to heart rate and heart rate variability, the subject is determined to be not wearing the sensor when no heart rate or heart rate variability is detected, while the monitoring of physical activities indicates sedentary behavior. Notably, the determination of whether the sensor is being worn by the subject may also be made when the monitoring of the physical activities indicates movement. This would detect a situation in which the subject may be physically carrying or transporting the sensor without actually wearing it, or in which the subject is wearing the sensor but the sensor is malfunctioning in regard to detecting and/or determining heart related information (which would still be treated as a determination of the sensor not being worn, as a practical matter).

When it is determined that the sensor is not being worn by the subject (block S414: No), one or more notifications may be provided to prompt the subject to wear the sensor in block S415 and to a monitoring system to prompt an appropriate response to the subject not wearing the sensor in block S416. For example, the notification in block S415 may include causing the sensor to provide an audible indication (e.g., chiming or buzzing) and/or a tactile indication (e.g., vibrating) to gain the attention of the subject and/or a caregiver. Notably, the caregiver may be remotely located relative to the user, and receive the notifications about wearing compliance. The contact in block S416 may include sending an indication to the effect that the subject is not wearing the sensor to one or more monitoring systems, such as an emergency dispatch center (e.g., a 911 call center), a PERS service center, and/or a computer, cellular phone, or other networked device of a caregiver, as discussed above. The indication warns the caregiver or other monitoring entity that the subject currently is not wearing the sensor. This may prompt follow-up action, such as questioning the subject and/or contacting the subject by phone to wear the sensor. The process then returns to block S411, and thus continues to attempt to monitor physical activities and to acquire and analyze heart sounds for determining whether the sensor is being worn.

When it is determined that the sensor is being worn by the subject (block S414: Yes), a process for performing activity monitoring and fall detection may be performed in block S417. This process may be performed, for example, according to the embodiment depicted in FIG. 2, although other processes for performing activity monitoring and fall detection may be incorporated, without departing from the scope of the present teachings. For example, the illustrative process for physical activity monitoring and wear detection of a wearable sensor depends on the detection of heart sounds, and not on the detection of audible trauma-related cues indicating pain levels suffered by the subject following a detected fall event, as discussed above with reference to FIG. 2. Accordingly, in an embodiment, the process for performing activity monitoring and fall detection performed in block S417 may include steps for determining whether a detected fall event is an actual fall and estimating the pain-level of the fallen subject relying on detected heart related information, without ambient sound detection that would otherwise isolate sound signals made by the subject following a detected fall event and extract sound segments corresponding to audible trauma-related cues from these isolated sound signals.

For example, in an embodiment, confirming the occurrence of an actual fall and estimating the pain-level the subject and/or the severity of the actual fall may be accomplished using just the determined heart rate (e.g., increased heart rate is consistent with an actual fall) and/or heart rate variability (e.g., decreased heart rate variability is consistent with an actual fall), in combination with the initial IMU fall detection. That is, the detected apparent fall may be determined to be an actual fall when the heart rate of the subject exceeds a predetermined heart rate baseline and/or when the heart rate variability of the subject falls below a predetermined heart rate variability threshold. This is because it is anticipated that the subject would maintain an unusually high, steady heart rate immediately following an actual fall.

Figure 5:
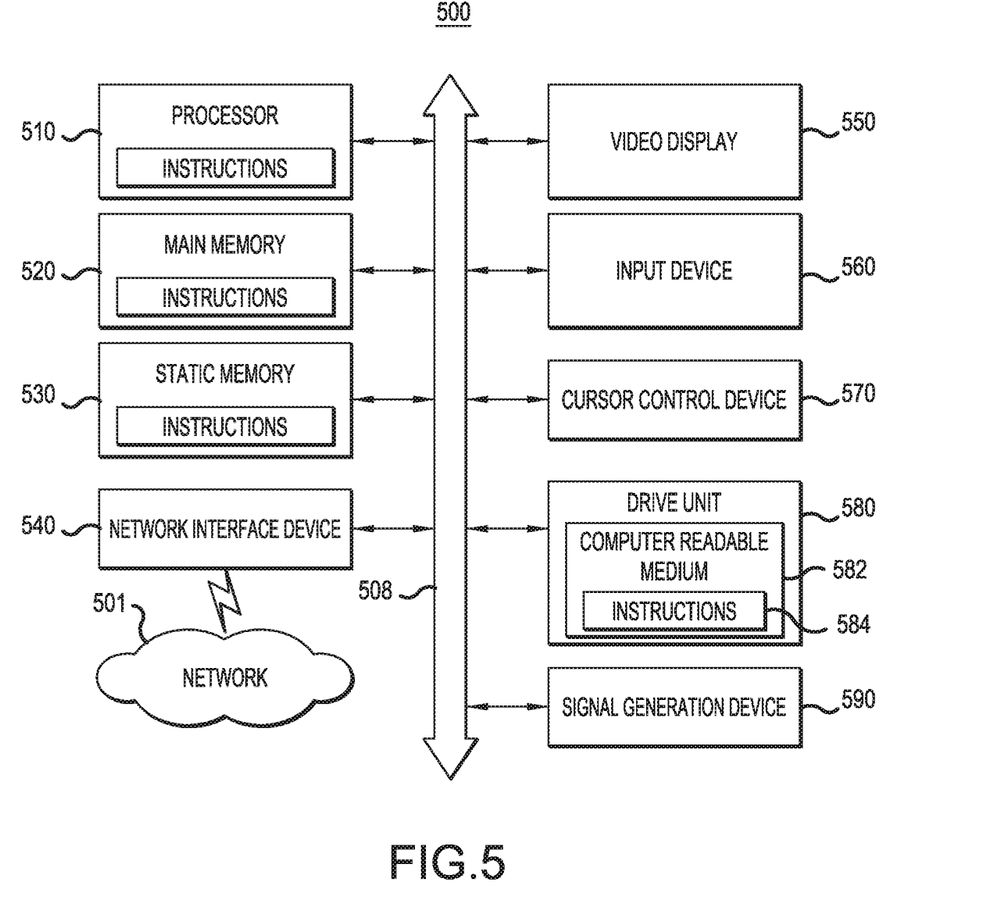
FIG. 5 illustrates a general computer system, on which a method of activity monitoring and fall detection of a subject using a wearable sensor may be implemented, in accordance with a representative embodiment.

FIG. 5 illustrates a general computer system, on which methods of monitoring physical activity, detecting whether a sensor is worn, and detecting falls a subject using the wearable sensor may be implemented, in accordance with a representative embodiment.

Referring to FIG. 5, computer system 500 can include a set of instructions that can be executed to cause the computer system 500 to perform any one or more of the methods or computer-based functions disclosed herein. The computer system 500 may operate as a standalone device or may be connected, for example, using a network 301, to other computer systems or peripheral devices.

In a networked deployment, the computer system 500 may operate in the capacity of a server or as a client user computer in a server-client user network environment, or as a peer computer system in a peer-to-peer (or distributed) network environment. The computer system 500 can also be implemented as or incorporated into various devices, such as a stationary computer, a mobile computer, a personal computer (PC), a laptop computer, a tablet computer, a wireless smart phone, a personal digital assistant (PDA), or any other machine capable of executing a set of instructions (sequential or otherwise) that specify actions to be taken by that machine. The computer system 500 may be incorporated as or in a device that in turn is in an integrated system that includes additional devices. In an embodiment, the computer system 500 can be implemented using electronic devices that provide voice, video or data communication. Further, while the computer system 500 is illustrated in the singular, the term "system" shall also be taken to include any collection of systems or sub-systems that individually or jointly execute a set, or multiple sets, of instructions to perform one or more computer functions.

As illustrated in FIG. 5, the computer system 500 includes a processor 510, which is tangible and non-transitory, and is representative of one or more processors. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A processor is an article of manufacture and/or a machine component. The processor 510 for the computer system 500 is configured to execute software instructions to perform functions as described in the various embodiments herein. The processor 510 may be a general-purpose processor or may be part of an application specific integrated circuit (ASIC). The processor 510 may also be (or include) a microprocessor, a microcomputer, a processor chip, a controller, a microcontroller, a digital signal processor (DSP), a state machine, or a programmable logic device. The processor 510 may also be (or include) a logical circuit, including a programmable gate array (PGA) such as a field programmable gate array (FPGA), or another type of circuit that includes discrete gate and/or transistor logic. The processor 510 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 500 may include a main memory 520 and/or a static memory 530, where the memories may communicate with each other via a bus 508. Memories described herein are tangible storage mediums that can store data and executable instructions and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 500 may further include a video display unit 550, such as a liquid crystal display (LCD), an organic light emitting diode (OLED), a flat panel display, a solid-state display, or a cathode ray tube (CRT). Additionally, the computer system 500 may include an input device 560, such as a keyboard/virtual keyboard or touch-sensitive input screen or speech input with speech recognition, and a cursor control device 570, such as a mouse or touch-sensitive input screen or pad. The computer system 500 can also include a disk drive unit 580, a signal generation device 590, such as a speaker or remote control, and a network interface device 540.

In an embodiment, as depicted in FIG. 5, the disk drive unit 580 may include a computer-readable medium 582 in which one or more sets of instructions 584, e.g. software, can be embedded. Sets of instructions 584 can be read from the computer-readable medium 582. Further, the instructions 584, when executed by a processor, can be used to perform one or more of the methods and processes as described herein. In an embodiment, the instructions 584 may reside completely, or at least partially, within the main memory 520, the static memory 530, and/or within the processor 510 during execution by the computer system 500.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 582 that includes instructions 584 or receives and executes instructions 584 responsive to a propagated signal; so that a device connected to a network 501 can communicate voice, video or data over the network 501. Further, the instructions 584 may be transmitted or received over the network 501 via the network interface device 540.

As described above, the present disclosure is not to be limited in terms of the particular embodiments described in this application, which are intended as illustrations of various aspects. Many modifications and variations can be made without departing from its spirit and scope, as may be apparent. Functionally equivalent methods and apparatuses within the scope of the disclosure, in addition to those enumerated herein, may be apparent from the foregoing representative descriptions. Such modifications and variations are intended to fall within the scope of the appended representative claims. The present disclosure is to be limited only by the terms of the appended representative claims, along with the full scope of equivalents to which such representative claims are entitled. It is also to be understood that the terminology used herein is for the purpose of describing particular embodiments only and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It may be understood by those within the art that terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It may be further understood by those within the art that if a specific number of an introduced claim recitation is intended, such an intent may be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It may be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" may be understood to include the possibilities of "A" or "B" or "A and B."

The foregoing description, along with its associated embodiments, has been presented for purposes of illustration only. It is not exhaustive and does not limit the concepts disclosed herein to their precise form disclosed. Those skilled in the art may appreciate from the foregoing description that modifications and variations are possible in light of the above teachings or may be acquired from practicing the disclosed embodiments. For example, the steps described need not be performed in the same sequence discussed or with the same degree of separation. Likewise various steps may be omitted, repeated, or combined, as necessary, to achieve the same or similar objectives. Accordingly, the present disclosure is not limited to the above-described embodiments, but instead is defined by the appended claims in light of their full scope of equivalents.

In the preceding, various preferred embodiments have been described with references to the accompanying drawings. It may, however, be evident that various modifications and changes may be made thereto, and additional embodiments may be implemented, without departing from the broader scope of the inventive concepts disclosed herein as set forth in the claims that follow. The specification and drawings are accordingly to be regarded as an illustrative rather than restrictive sense.

Although system and method of physical activity monitoring of a subject, as well as sensor wear detection and subject fall detection, using a wearable sensor, have been described with reference to a number of illustrative embodiments, it is understood that the words that have been used are words of description and illustration, rather than words of limitation. Changes may be made within the purview of the appended claims, as presently stated and as amended, without departing from the scope and spirit of system and method of optimal sensor placement in its aspects. Although system and method of optimal sensor placement has been described with reference to particular means, materials and embodiments, system and method of optimal sensor placement is not intended to be limited to the particulars disclosed; rather system and method of evaluating a subject using a wearable sensor extend to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A method of performing physical activity monitoring and fall detection of a subject using a wearable sensor comprising at least one audio sensor and at least one of: an accelerometer, a gyroscope, and a magnetometer, the method comprising:

monitoring activities of the subject using the at least one of: the accelerometer, the gyroscope, and the magnetometer, and identifying at least one characteristic motion pattern based on the monitored activities;

detecting an apparent fall experienced by the subject based on the identified at least one characteristic motion pattern;

monitoring sounds provided by the at least one audio sensor following the detected apparent fall;

determining whether the detected apparent fall is an actual fall experienced by isolating sound signals produced by the subject and provided by the at least one audio sensor using a predetermined model tuned to an acoustic profile of the subject;

extracting segments corresponding to audible trauma-related cues from the isolated sound signals using a gated recurrent neural network with bi-directional long short-term memory (LSTM); and determining that the detected apparent fall is an actual fall based on the extracted segments communicating an indication of the actual fall to a monitoring system, enabling commencement of responsive action.

2. The method of claim 1, wherein the audible trauma-related cues comprise one or more of abnormal breathing, sighing, moaning, groaning, grunting, crying and/or verbal expression of having fallen or being injured.

3. The method of claim 1, further comprising:
when it is determined that the detected apparent fall is an actual fall, estimating an extent of pain sustained by the subject based on the audible trauma-related cues, and communicating an indication of the actual fall and the extent of pain to the monitoring system.

4. The method of claim 1, wherein extracting segments corresponding to audible trauma-related cues from the isolated sound signals comprises:
extracting oral, linguistic, and paralinguistic cues from the isolated sound signals; and
estimating a level of pain of the subject based on the extracted oral, linguistic and paralinguistic cues, together with a determined heart rate of the subject,
wherein the detected apparent fall is determined to be an actual fall when the level of pain exceeds a predetermined threshold.

5. The method of claim 1, further comprising:
determining at least one of a heart rate of the subject, a heart rate variability of the subject and a heart sound quality based on the monitored sounds provided by the at least one audio sensor, determining whether the detected apparent fall is an actual fall is based on the heart rate of the subject exceeding a predetermined heart rate baseline and/or the heart rate variability of the subject falling below a predetermined heart rate variability baseline.

6. The method of claim 5, further comprising:
determining whether the subject is wearing the sensor based on at least one of the determined heart rate, the determined heart rate variability, and the determined heart sound quality.

7. The method of claim 6, further comprising:
notifying the subject and/or the monitoring system when it is determined that the subject is not wearing the sensor to prompt the subject to wear the sensor.

8. The method of claim 6, wherein the detected apparent fall is determined to be an actual fall when the determined heart rate increases and/or the determined heart rate variability decreases as compared to the predetermined baselines, respectively.

9. A sensor system, including a sensor wearable on a body of a subject, for monitoring physical activity of the subject, the system comprising:
   an inertial measurement unit that monitors physical movements of the subject;
   at least one audio sensor that detects ambient sounds around the subject;
   a memory that stores executable instructions comprising a fall detection module, a post-fall sound acquisition module, a sound-driven fall detection confirmation module, a sound-driven pain level assessment module, and a sound segmentation module;
   a processor that executes the instructions retrieved from the memory, wherein the instructions, when executed, cause the processor to:
      detect an apparent fall experienced by the subject, based on the physical activities of the subject monitored by the inertial measurement unit, in accordance with the fall detection module;
      acquire sounds provided by the at least one audio sensor following the detected apparent fall in accordance with the post-fall sound acquisition module;
      isolate sound signals produced by the subject using a predetermined model tuned to an acoustic profile of the subject, and extract segments corresponding to audible trauma-related cues from the isolated sound signals using a gated recurrent neural network with bi-directional long short-term memory (LSTM), in accordance with the sound segmentation module;
      determine that the detected apparent fall is an actual fall experienced by the subject based on the acquired sounds in accordance with the sound-driven fall detection confirmation module; and
      estimate a level of pain of the subject based on the audible trauma-related cues produced by the subject and extracted from the acquired sounds in accordance with the sound-driven pain level assessment module; and
   a communication interface that communicates an indication of the actual fall to a monitoring system over a wireless network, enabling commencement of responsive action.

10. The system of claim 9, wherein the memory that stores executable instructions further comprises a heart sound detection module, and wherein the instructions, when executed, further cause the processor to:
   determine at least one of a heart rate of the subject, a heart rate variability of the subject and a heart sound quality based on the acquired sounds in accordance with the heart sound detection module.

11. The system of claim 10, wherein the memory that stores executable instructions further comprises a wear detection module, and wherein the instructions, when executed, further cause the processor to:
   determine whether the sensor is being worn by the subject based on the physical activities of the subject monitored by the inertial measurement unit and the determined heart sound quality in accordance with the wear detection module.

12. A non-transitory machine-readable storage medium encoded with instructions for performing physical activity monitoring and fall detection of a subject using a wearable sensor comprising at least one audio sensor and at least one of an accelerometer, a gyroscope, and a magnetometer, wherein the instructions comprise:
   instructions for monitoring activities of the subject using the at least one of: the accelerometer, the gyroscope, and the magnetometer, and identifying at least one characteristic motion pattern based on the monitored activities;
   instructions for detecting an apparent fall experienced by the subject based on the identified at least one characteristic motion pattern;
   instructions for monitoring sounds provided by the at least one audio sensor following the detected apparent fall;
   instructions for determining whether the detected apparent fall is an actual fall experienced by isolating sound signals produced by the subject and provided by the at least one audio sensor using a predetermined model tuned to an acoustic profile of the subject;
   instructions for extracting segments corresponding to audible trauma-related cues from the isolated sound signals using a gated recurrent neural network with bi-directional long short-term memory (LSTM); and
   instructions for determining that the detected apparent fall is an actual fall based on the extracted segments;
   instructions for communicating an indication of the actual fall to a monitoring system, enabling commencement of responsive action.

13. The non-transitory machine-readable storage medium of claim 12, wherein the audible trauma-related cues comprise one or more of abnormal breathing, sighing, moaning, groaning, grunting, crying and/or verbal expression of having fallen or being injured.

14. The non-transitory machine-readable storage medium of claim 12, further comprising instructions for when it is determined that the detected apparent fall is an actual fall, estimating an extent of pain sustained by the subject based on the audible trauma-related cues, and communicating an indication of the actual fall and the extent of pain to the monitoring system.

15. The non-transitory machine-readable storage medium of claim 12, wherein instructions for extracting segments corresponding to audible trauma-related cues from the isolated sound signals comprises:
   instructions for extracting oral, linguistic, and paralinguistic cues from the isolated sound signals; and
   instructions for estimating a level of pain of the subject based on the extracted oral, linguistic and paralinguistic cues, together with a determined heart rate of the subject,
   wherein the detected apparent fall is determined to be an actual fall when the level of pain exceeds a predetermined threshold.

16. The non-transitory machine-readable storage medium of claim 12, further comprising instructions for determining at least one of a heart rate of the subject, a heart rate variability of the subject and a heart sound quality based on the monitored sounds provided by the at least one audio sensor, determining whether the detected apparent fall is an actual fall is based on the heart rate of the subject exceeding a predetermined heart rate baseline and/or the heart rate variability of the subject falling below a predetermined heart rate variability baseline.

17. The non-transitory machine-readable storage medium of claim 16, further comprising instructions for determining whether the subject is wearing the sensor based on at least one of the determined heart rate, the determined heart rate variability, and the determined heart sound quality.

18. The non-transitory machine-readable storage medium of claim 17, further comprising instructions for notifying the subject and/or the monitoring system when it is determined that the subject is not wearing the sensor to prompt the subject to wear the sensor.

\* \* \* \* \*